United States Patent [19]

Emanuel

[11] Patent Number: 5,554,122
[45] Date of Patent: Sep. 10, 1996

[54] DISPOSABLE SYRINGE

[76] Inventor: Carolina Emanuel, 165 Staples Rd., Easton, Conn. 06612

[21] Appl. No.: 411,141

[22] Filed: Mar. 23, 1995

[51] Int. Cl.⁶ .................................................. A61M 5/00
[52] U.S. Cl. ........................... 604/110; 604/198; 604/263
[58] Field of Search ..................................... 604/110, 187, 604/192, 198, 263

[56] References Cited

U.S. PATENT DOCUMENTS

| | | | |
|---|---|---|---|
| 4,693,708 | 9/1987 | Wanderer et al. ................... | 604/263 X |
| 4,723,943 | 2/1988 | Spencer ..................................... | 604/198 |
| 4,743,233 | 5/1988 | Schneider ................................ | 604/192 |
| 5,057,089 | 10/1991 | Greco ........................................ | 604/198 |

Primary Examiner—John D. Yasko
Attorney, Agent, or Firm—Klein & Vibber P.C.

[57] ABSTRACT

A disposable syringe comprising two slidably collapsible cylindrical portions. The first cylindrical portion forms part of a standard disposable syringe which has been slightly altered to include one or more integral protrusions. The second cylindrical portion is slidably movable along the first cylindrical portion from an extended position in which it completely envelopes the needle portion of the disposable syringe to a retracted position in which the needle is fully exposed. Means are provided on the two cylindrical portions to prevent the retraction of the second cylindrical portion after the disposable syringe has been used so as to prevent any reuse of the disposable syringe.

5 Claims, 10 Drawing Sheets

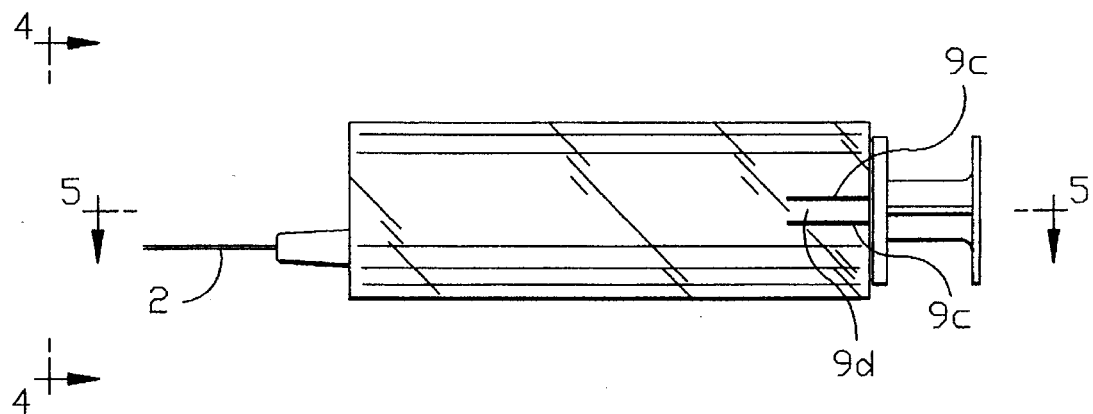
FIG. 1
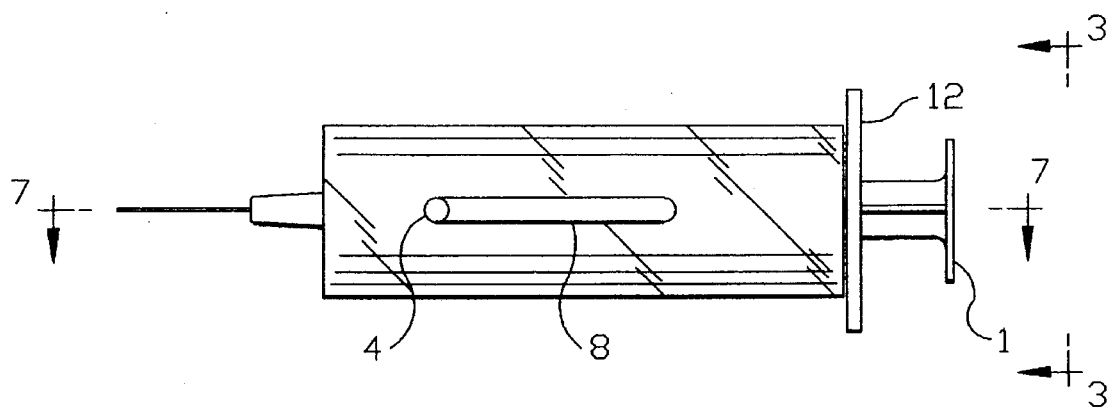
FIG. 2
FIG. 3
FIG. 4
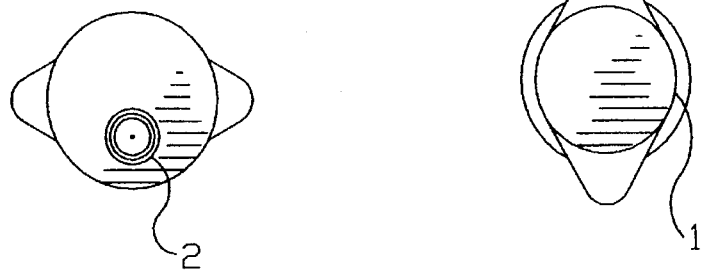

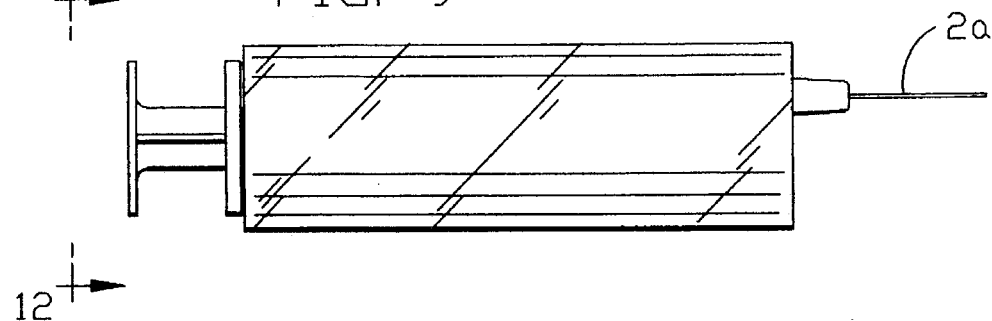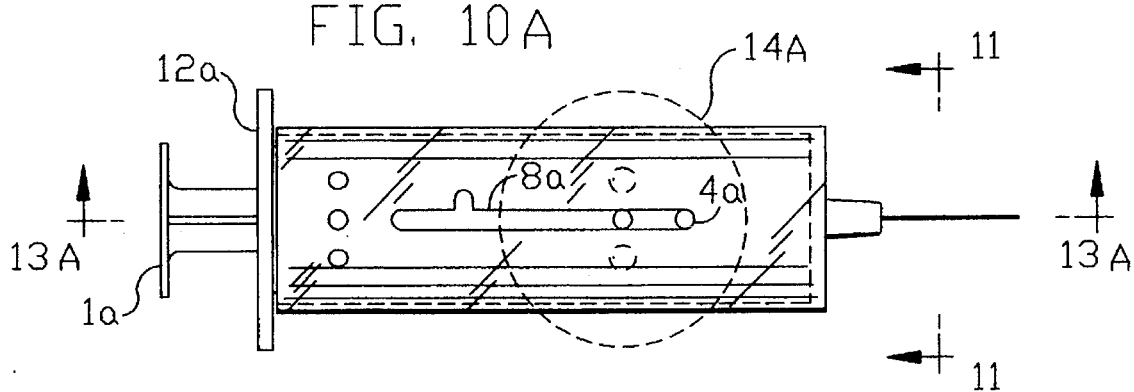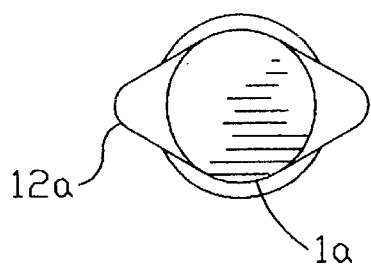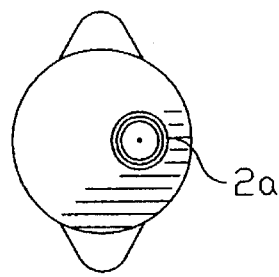

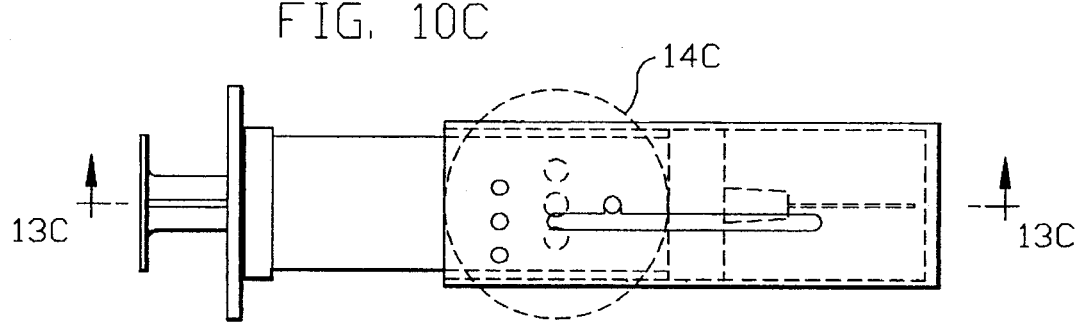
FIG. 10C
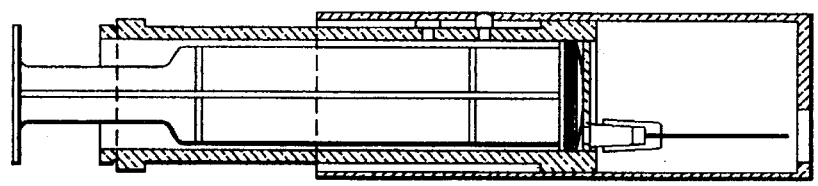
FIG. 13C
FIG. 14C
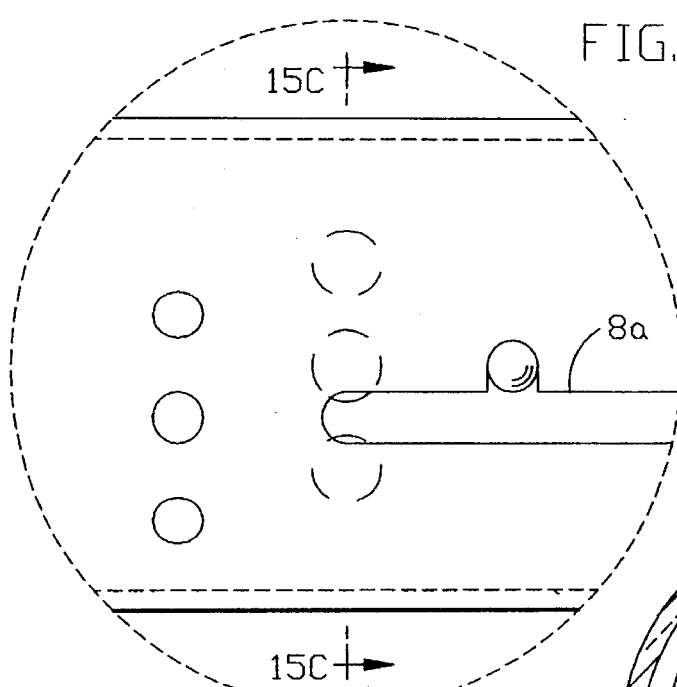
FIG. 15C
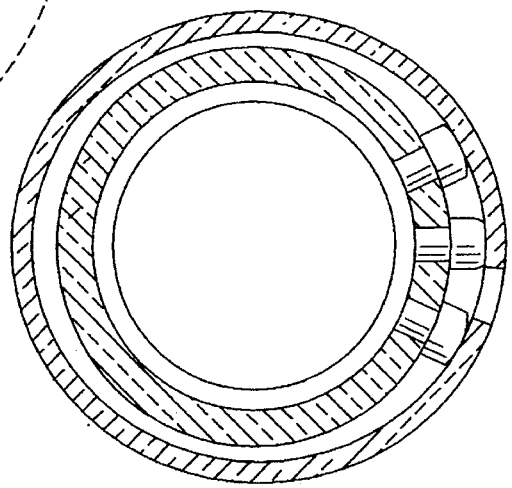

DISPOSABLE SYRINGE

BACKGROUND OF THE INVENTION

The invention relates to a disposable syringe which is more tamper proof and safe than the disposable syringes of the state of the art. At present there exists an ever increasing risk of exposure to contaminated needles of disposable syringes. Such needles may at times even carry infectious material of life threatening diseases. There is always a risk of infection present with the state of the art disposable syringe because the needle is exposed before and after use by the person handling the disposable syringe and therefore is capable of accidentally pricking this person. Therefore, the risk of being accidentally pricked by the exposed needle during the handling of the state of the art syringe is an ever present danger. Furthermore, even after use of the state of the art syringe, there still exists the risk of accidental exposure of infectious material by those handling the waste material, i.e. being pricked by the used needle forming part of the waste material. The state of the art method of capping, closing or concealing the used, i.e. "contaminated" needle requires accuracy and caution while still presenting a considerable potential risk of accidental pricking.

SUMMARY OF THE INVENTION

The object of the invention is to provide a disposable tamper-proof hypodermic syringe the use of which has the following advantages:

a) the risk of being accidentally pricked by the syringe during use is eliminated;

b) the risk of accidentally being pricked after use and disposal of the syringe is eliminated;

c) the improved disposable syringe of the invention is tamper proof because the novel syringe construction of the invention virtually prevents a re-use of the hypodermic syringe; and d) the disposable of the improved syringe is safer and more sanitary because the needle is, immediately after use, completely enveloped in a self contained protective cylindrical cover which is locked in position thereby preventing accidental contact with the used syringe needle.

These advantages and objects of the improved disposable syringe of the invention include the distinct advantage that the novel syringe reduces the anxiety associated with using state of the art disposable syringes with, for example, HIV positive patients because the risk of accidental pricking is virtually eliminated. For home users of disposable syringes the invention provides a simple sanitary method of disposing of bio-hazardous waste. The syringe of the invention can also be used with plastic intravenous (IV) feed lines. The danger of accidentally transmitting any blood transferred infectious material is virtually eliminated.

The novel improved construction of the hypodermic syringe of the invention indicates clearly to the prospective user whether the syringe had been tampered with prior to use even when the protective plastic cover has been accidentally torn or when no protective cover or sheathing is present. The invention ensures that a new, sanitary, unused needle is being used with each broken seal of the plastic cover of when no cover is present. The seal usually is a plastic cover which can easily be torn open. Most seals are formed by a plastic hermetically sealed plastic cover which maintains the syringe in a sterile condition prior to use and has a weakened portion such as a groove to facilitate the tearing of the plastic cover immediately prior to use.

The novel hypodermic syringe construction of the invention includes two cylindrical collapsible parts. A first cylindrical part forms part of a standard syringe construction which has been slightly modified in accordance with the invention to include at least one protrusion which is preferably integral with the first cylindrical portion and which can be manufactured by means of conventional injection molding techniques. This protrusion serves as a guide and/or locking means to guide or maintained the second cylindrical portion in an extended position in which is completely envelopes the needle of the syringe. This second cylindrical portion acts as a protective cover, when it is in an extended locked position, and thus protects family and children and sanitation workers, who collect and dispose of waste products, from accidentally pricking themselves. The disposable syringe may therefore, when the second cylindrical portion or cover is in the extended locked position, be safely tossed away with common garbage since the safety mechanism is entirely self-contained and there is no longer any risk of accidental physical contact with the syringe needle.

In a first embodiment of the invention the second cylindrical portion, which snugly envelopes the first cylindrical portion but is manually slidable therealong, is initially in the retracted position. In this position the needle is, prior to use, covered by the conventional plastic cap and the syringe is enclosed in a hermetically sealed sheath or cover. When the syringe is to be used the plastic sheath or cover is torn and the plastic cap is removed. The syringe is now ready for use. After the syringe has been used, the second cylindrical portion is manually slid forward into a fully extended position in which the needle is fully enveloped so that no accidental pricking can occur. Locking means are provided on the first and second cylindrical portions which interlock in the fully extended position and ensure that the second cylindrical portion can not again be retracted from its fully extended position. The syringe is now safe to be disposed of by conventional medical waste disposable methods.

In a second embodiment of the invention, the second cylindrical portion, which snugly envelopes the first cylindrical portion but is slidable therealong, is initially in a first semi-extended position. The syringe is preferably packaged in a thin plastic sheath or cover prior to use when it is in this semi-extended position. In this initial semi-extended position the needle does not require the conventional plastic cap cover because the needle is already prior to use fully enveloped by the second cylindrical portion so that no accidental pricking can occur. The second cylindrical portion is held in this initial semi-extended position by means of a short circumferentially extending slot into which a first protrusion, of a plurality of integral protrusions on the first cylindrical portion, projects. By means of a small angle turn of the two cylindrical portions relative to each other the first protrusion is moved out of this short circumferentially extending slot and into a second longitudinal extending slot which is parallel to the axes of the first and second cylindrical portions. The second cylindrical portion is now ready to be fully retracted into a second operative position in which the needle is fully exposed and ready to be used. After the needle has been used, the second cylindrical portion is slidably moved forward on the first cylindrical portion into a third fully extended position. The slidable forward movement stops when a plurality of semi-elastic integral protrusions on the first cylindrical portion snap into mating openings in the second cylindrical portion to permanently lock the second cylindrical portion in the fully extended third position. In this third position the needle is also fully enveloped by the second cylindrical portion to prevent any accidental pricking and is ready to be thrown away.

BRIEF DESCRIPTION OF THE DRAWING

With these and other objects in view, which will become apparent in the following detailed description the present invention, which is shown by example only, will be clearly understood in connection with the accompanying drawing, in which:

FIG. 1 illustrates in side elevation a first embodiment of a disposable syringe in accordance with the invention;

FIG. 2 is a top plan view of the syringe illustrated in FIG. 1;

FIG. 3 is an end elevational view of the syringe illustrated in FIG. 1 at the end where the plunger of the syringe is located;

FIG. 4 is an end elevational view of the syringe illustrated in FIG. 1 at the end where the needle of the syringe is located;

FIG. 9 illustrates in side elevation a second embodiment of a disposable syringe in accordance with the invention;

FIG. 10A is a top plan view of the syringe illustrated in FIG. 9 in a first operative position;

FIG. 10C is a top plan view of the syringe illustrated in FIG. 9 in a third operative position;

FIG. 11 is an end elevational view of the syringe illustrated in FIG. 9 at the end where the needle of the syringe is located;

FIG. 12 is an end elevational view of the syringe illustrated in FIG. 9 at the end where the plunger of the syringe is located;

FIG. 13C is a cross-sectional view of the syringe FIG. 10C along line 13C—13C of FIG. 10C;

FIG. 14C is an enlarged detailed view of the area in the circle 14C of FIG. 10C;

FIG. 15C is a cross-sectional view along line 15C—15C of FIG. 14C;

DESCRIPTION OF THE PREFERRED EMBODIMENTS

First Embodiment

Figure 5A:
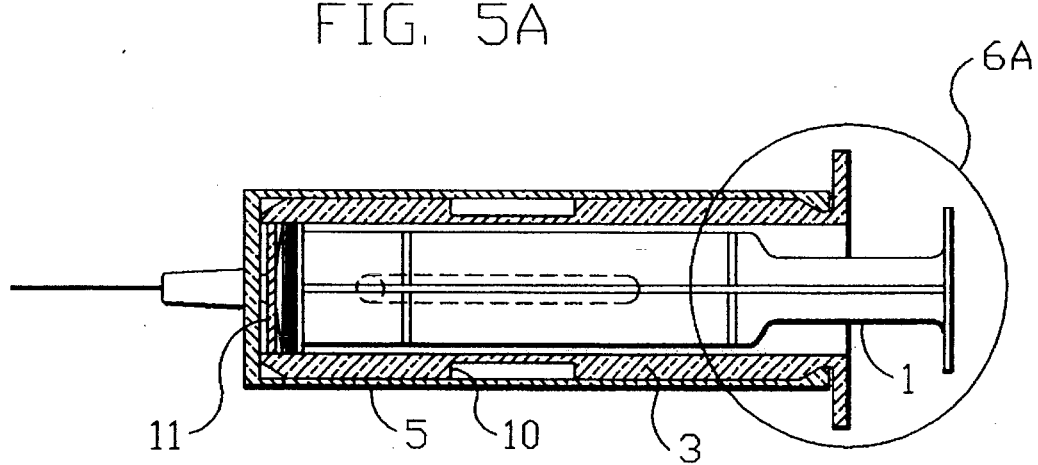
FIG. 5A is a cross-sectional view of the syringe along line 5—5 of FIG. 1 when the syringe is in a first operative position.
Figure 5B:
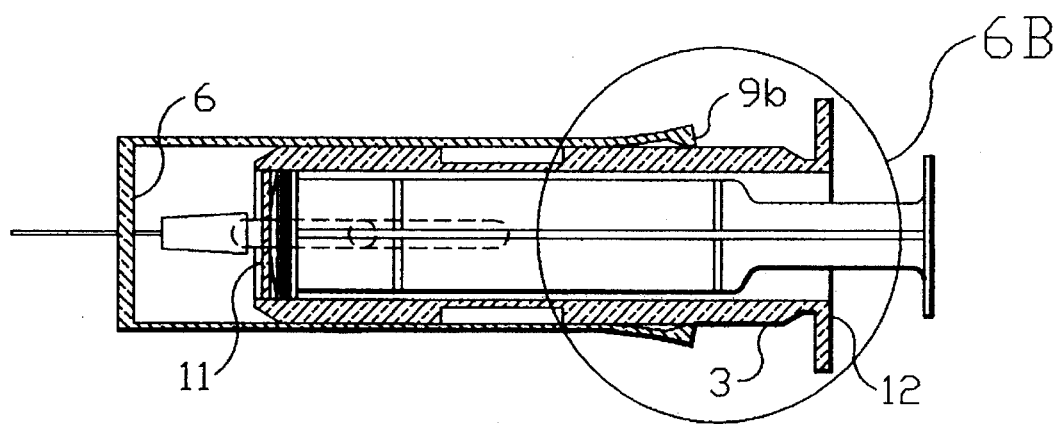
FIG. 5B is a cross-sectional view of the syringe along line 5—5 of FIG. 1 when the syringe is in a second operative position.

FIGS. 1 to 8 illustrate a first embodiment of the disposable syringe of the invention. As can be noted from FIGS. 1–4 the disposable syringe includes a conventional plunger 1 and a conventional needle 2, which is covered with a conventional plastic cap (not illustrated) prior to being used. The plunger or piston 1 is reciprocally mounted in a plastic cylinder 3 forming the so-called first cylindrical portion. At least one protrusion 4 is either integral with the first cylindrical portion or is firmly mounted in the first cylindrical portion. A second cylindrical portion 5 fits snugly around the first cylindrical portion 3 but is manually slidable therealong. This second cylindrical portion is made of a lighter polymer material than the first cylindrical portion 3 so that the second cylindrical portion 5 has a certain elasticity relative to the first cylindrical portion 3. The second cylindrical portion 5 has at least one longitudinal slot 8 which is parallel to the axes of the first and second cylindrical portions. The longitudinal slot 8 has a width which is slightly larger than the diameter of the protrusion 4 so that the second cylindrical portion can freely slide over the first cylindrical portion 3 while the protrusion 4 guides this movement. The slidable movement of the second cylindrical portion relative to the first cylindrical portion is limited by the longitudinal extent of longitudinal slot 8. The interaction of the protrusion 4 with the longitudinal slot 8 prevents also a relative rotational movement between the first and second cylindrical portions 3 and 5.

The second cylindrical portion 5 has at the end adjacent to the plunger 1 an inwardly projecting circular abutment or skirt 9B which matingly projects into an annular groove 9A in the first cylindrical portion 3. The second cylindrical portion 5 has at least a pair of diametrically opposite straps 9 which are formed by means of longitudinal slits 9C. The first cylindrical portion 3 has at least a pair of diametrically opposite slots 10 which are aligned with straps 9. The second cylindrical portion has a bottom 6 with an opening 7 which is sufficiently large to permit the needle 2 to project there through.

Manner of Operation of the First Embodiment

The disposable syringe of the first embodiment of the invention is usually provided with a plastic cap (not illustrated) and stored in a plastic sterile sealed container (not illustrated) prior to use. This inoperative position of the disposable syringe is illustrated in FIGS. 1, 2, 5A and 7. The syringe is then removed from the plastic container and the plunger 1 is manually depressed or retracted in the first cylindrical portion depending on whether liquid is to be dispensed or aspirated by the syringe. In the inoperative position the protuberance 4 is located at its most forward position relative to the longitudinal slot 8 so that the first cylindrical portion 3 can no longer be moved forward relative to the second cylindrical portion 5. This limit to the forward movement is also additionally provided by the abutting contact of the front face 11 of the syringe body and the end face 6 of the second cylindrical portion 5. Furthermore a limit to this forward movement is provided by the abutting contact between the skirt 9B and the platform or collar 12 of the syringe.

Figure 6A:
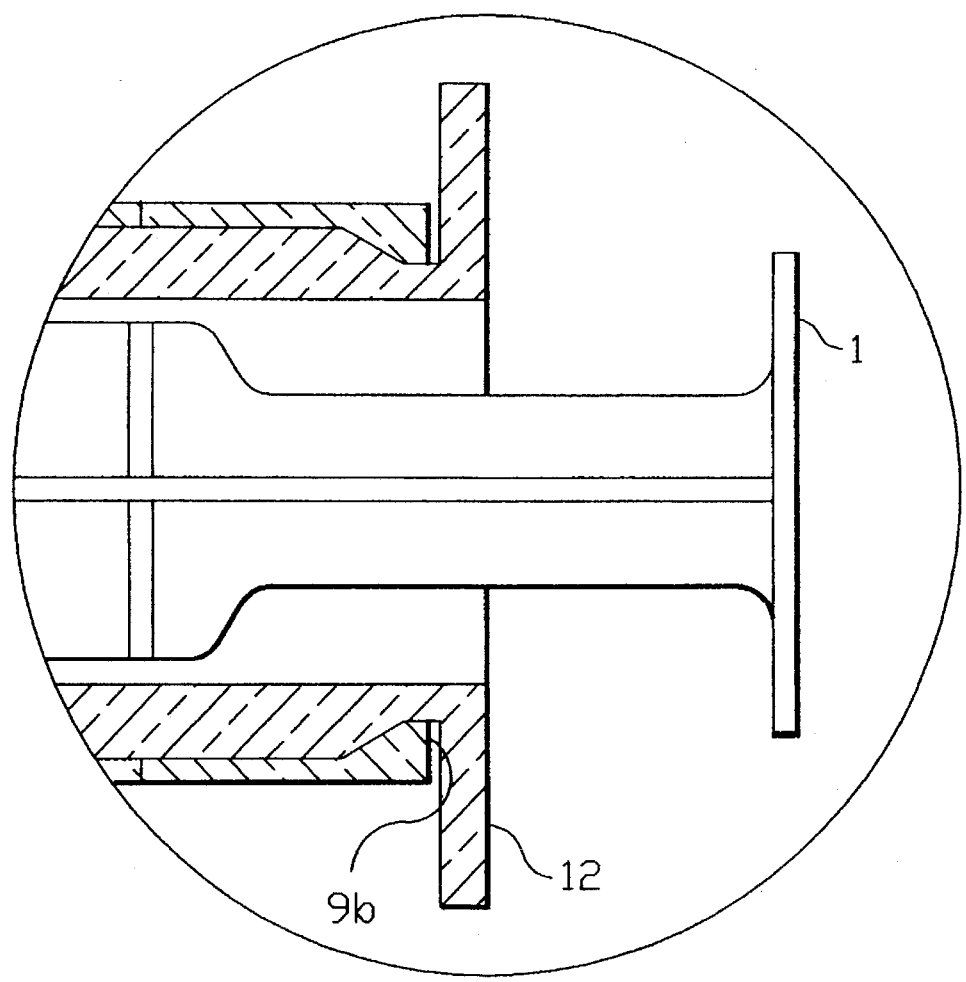
FIG. 6A is an enlarged detailed view of the area in the circle 6A in FIG. 5A.
Figure 6B:
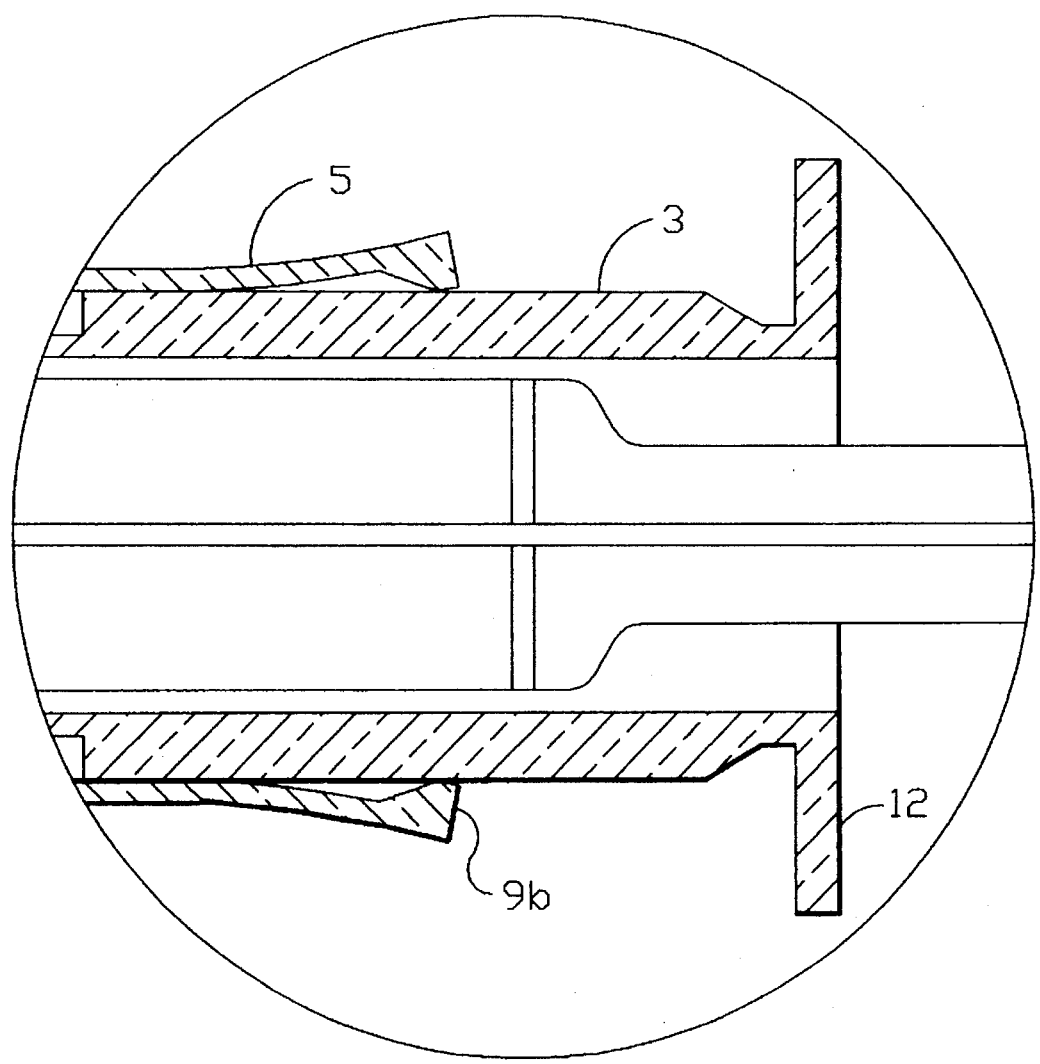
FIG. 6B is an enlarged detailed view of the area in the circle 6B in FIG. 5B.
Figure 5C:
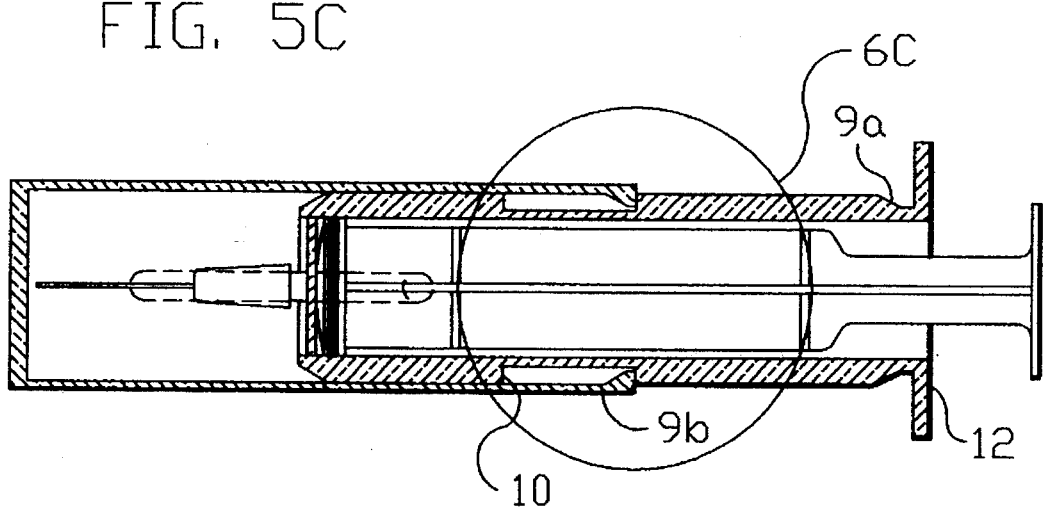
FIG. 5C is a cross-sectional view of the syringe along line 5—5 of FIG. 1 when the syringe is in a third operative position.
Figure 6C:
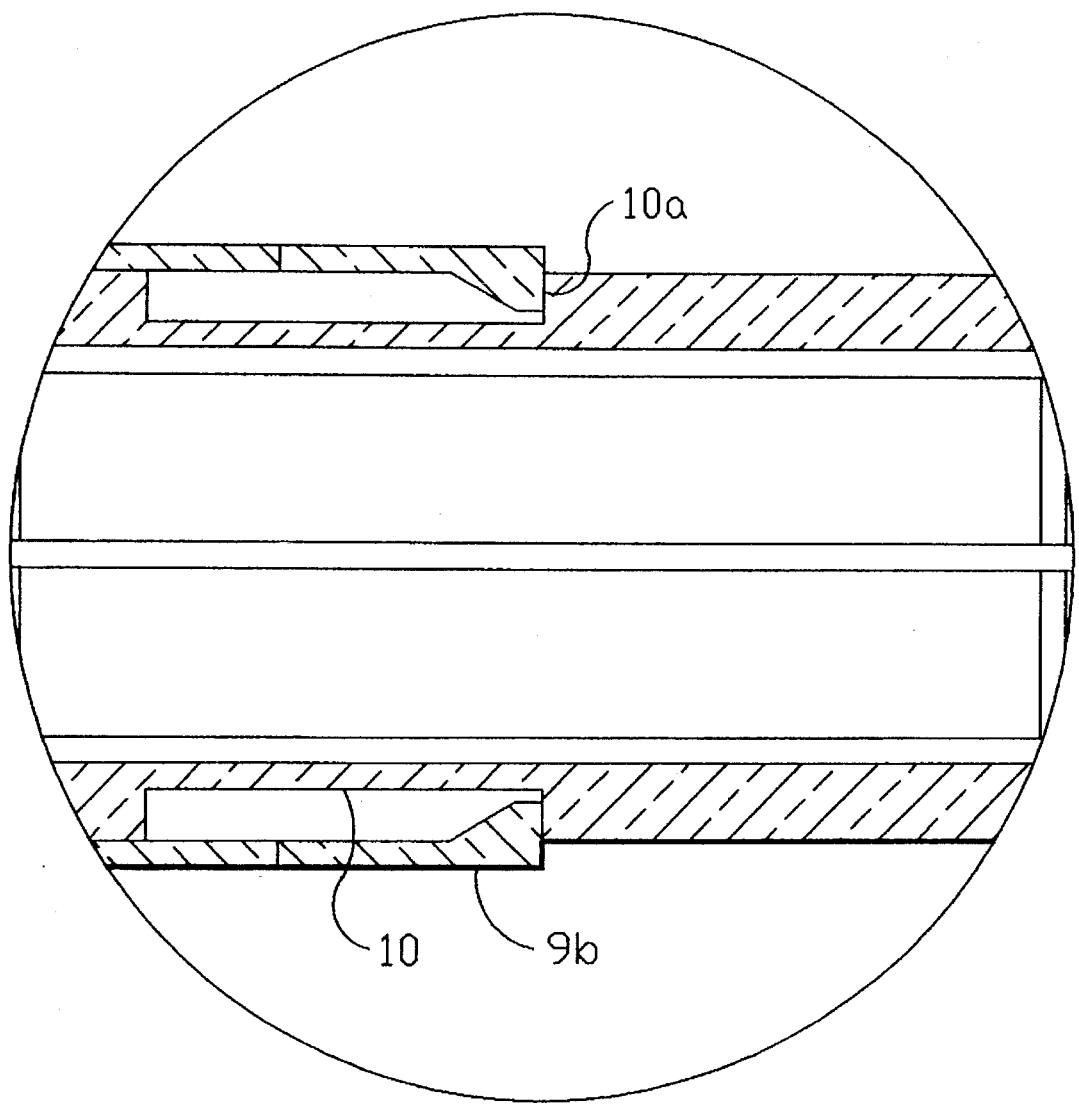
FIG. 6C is an enlarged detailed view of the area in the circle 6C in FIG. 5C.
Figure 7:
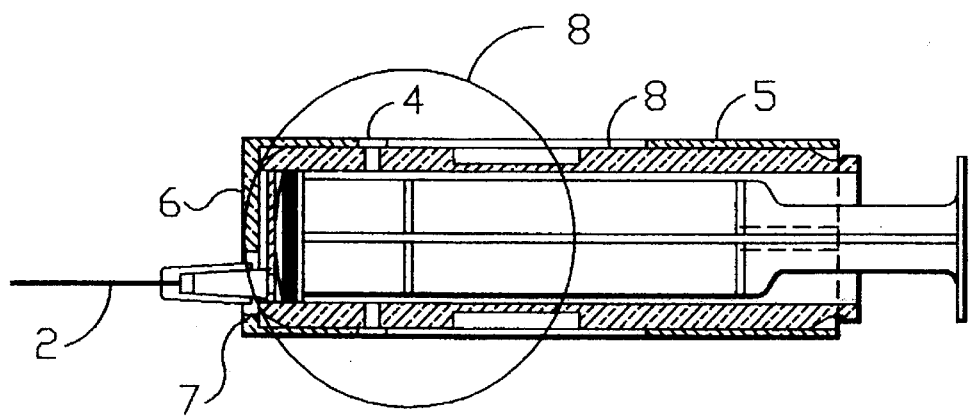
FIG. 7 is an other cross-sectional view of the syringe along line 7—7 of FIG. 2 when the syringe is in the first operative position.
Figure 8:
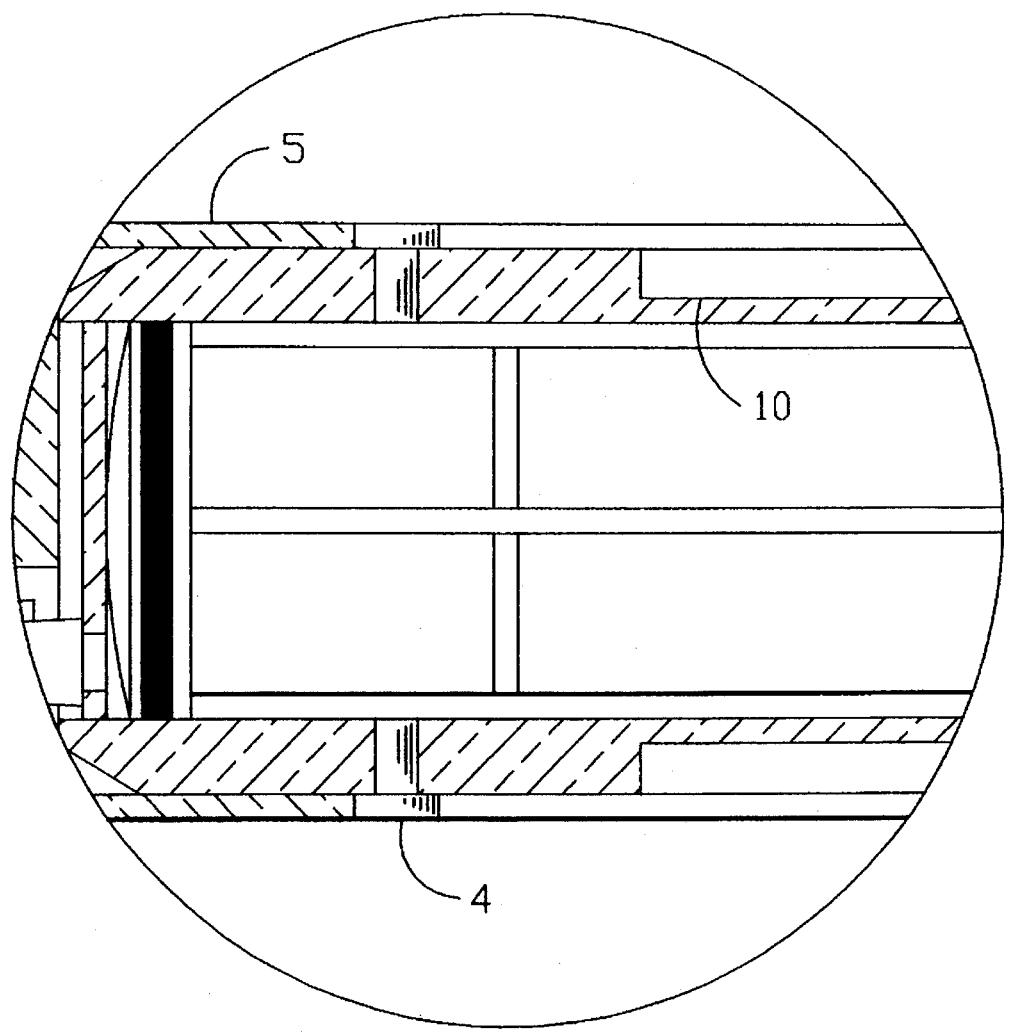
FIG. 8 is an enlarged detailed view of the of the area in the circle 8 of FIG. 7.
Figure 10B:
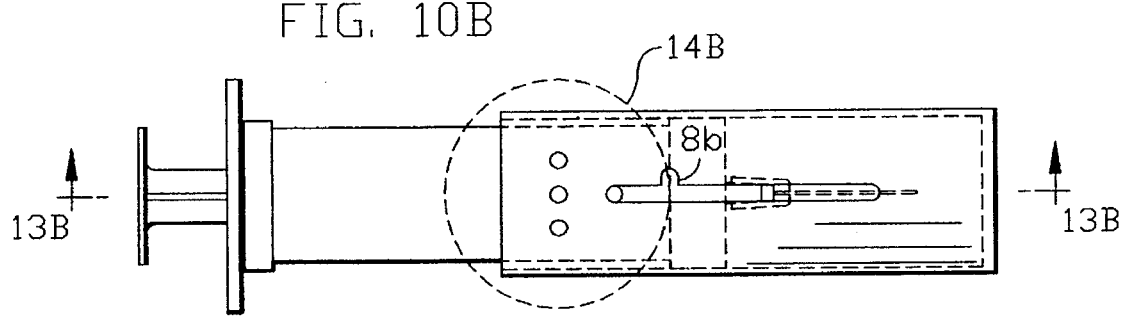
FIG. 10B is a top plan view of the syringe illustrated in FIG. 9 in a second operative position.
Figure 14B:
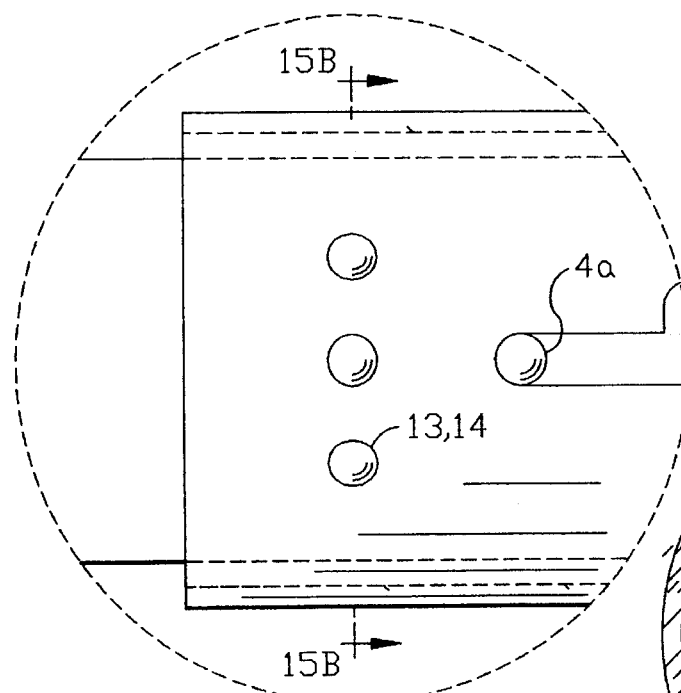
FIG. 14B is an enlarged detailed view of the area in the circle 14B of FIG. 10B.
Figure 15B:
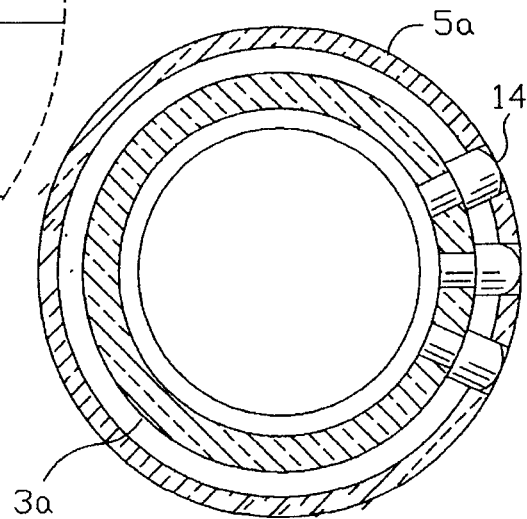
FIG. 15B is a cross-sectional view along line 15B—15B of FIG. of FIG. 14B.

After the syringe has been used as described above the second cylindrical portion 5 is manually moved forward relative to the first cylindrical portion 3 by firmly grasping the second cylindrical portion 5 with one hand and holding the platform or collar 12 with the other hand. The second cylindrical portion 5 is then pushed forward with sufficient force to cause the skirt or abutment 9B to move out of the annular groove 9A and slide over the cylindrical surface of the first cylindrical body 3. This operation is illustrated in FIGS. 5A and 6B. This forward movement of the second cylindrical portion 5 over the first cylindrical portion 3 continues until the pair of straps 9 snap into the longitudinal slots 10. This position of the assembly is illustrated in FIGS. 5C and 6C. The snapping inwardly of these straps 9 signals to the user of the syringe that it is now in a condition of being safely disposed of, i.e. thrown away. As can be seen in FIG. 5C, when the straps 9 have snapped into longitudinal slots 10 the needle 2 is fully enveloped by the second cylindrical portion 5 so that no risk of accidental pricking by the needle 2 is possible. Moreover, the second cylindrical portion 5 can no longer be retracted over the first cylindrical portion 3 because of the abutting contact between the rear end of each one of the pair of straps 9 with the rear wall 10A of the corresponding longitudinal slot 10. It will of course be evident to those skilled in the art that a larger number than just a pair of straps 9 and slots 10 can be provided. These straps 9 and slots 10 should be respectively equidistantly located around the peripheries of the second cylindrical and first cylindrical portions 3 and 5. The more straps 9 and slots 10 are provided, the easier the initial movement becomes of the second cylindrical portion 5 relative to the first cylindrical portion 3 because of reduced frictional contact and the more securely the rear walls 10A of the slots 10 prevent the retraction of the second cylindrical portion 5 from the position shown in FIG. 6C.

Second Embodiment

FIGS. 9 to 16D illustrate the second embodiment of the invention. As is illustrated in FIGS. 9 to 13C the second embodiment also includes first and second cylindrical portions. (Those elements in the second embodiment which are functionally equivalent or similar to the elements of the first embodiment have been designed with same reference numbers to which the small case letter "a" has been added).

Figure 13B:
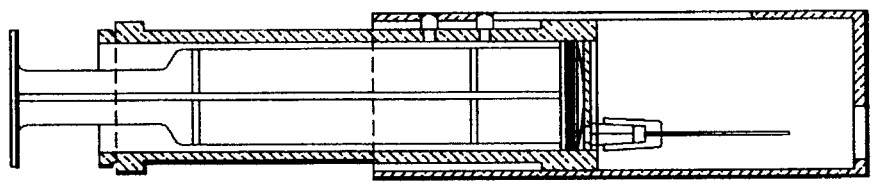
FIG. 13B is a cross-sectional view of the syringe along line 13B—13B of FIG. 10B.
Figure 13A:
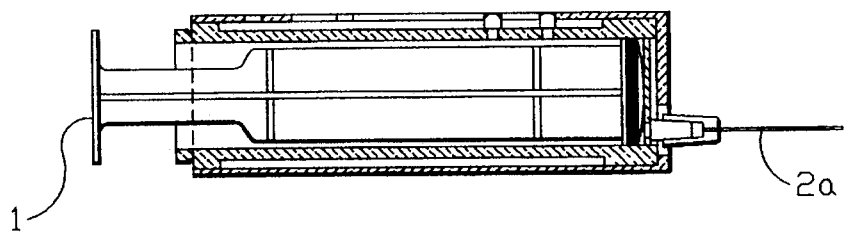
FIG. 13A is a cross-sectional view of the syringe illustrated in FIG. 10A along line 13A—13A.
Figure 14A:
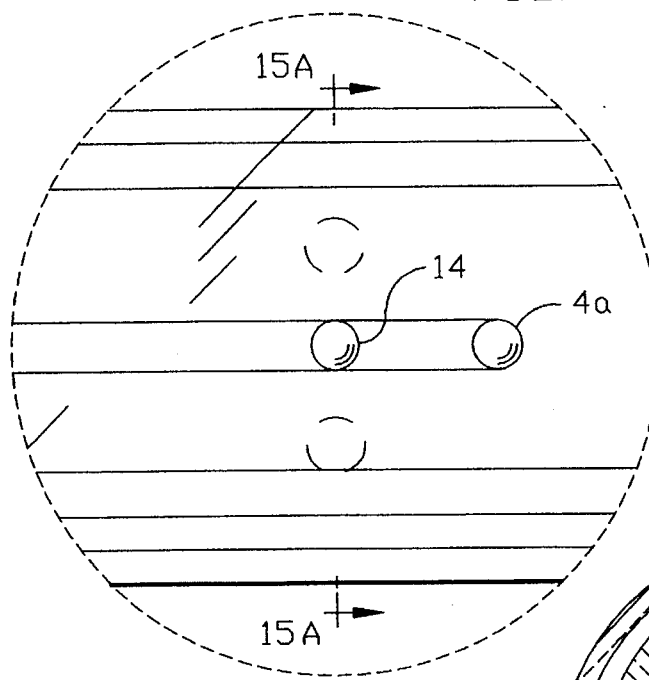
FIG. 14A is an enlarged detailed view oft he area in the circle 14A of FIG. 10A.
Figure 15A:
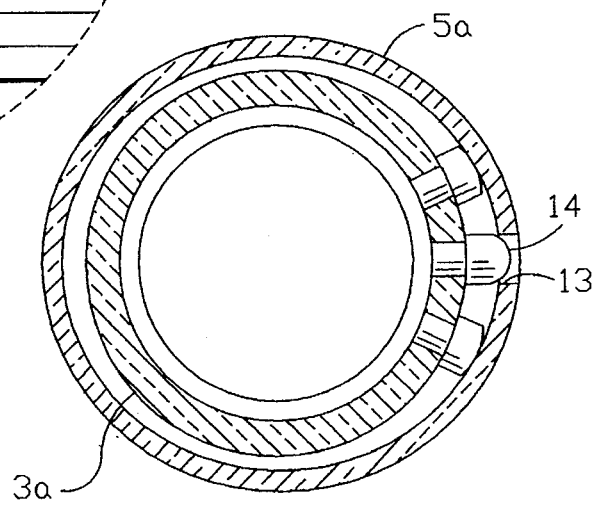
FIG. 15A is a cross-sectional view along line 15A—15A of FIG. 14A.

In this embodiment of the invention the second cylindrical portion 5a is mounted on two opposite collars projecting outwardly from the cylindrical portion 3a (FIG. 13A). Therefore there remains a small annular space of predetermined depth between the first and second cylindrical portions 3a, 5a. In addition to the flat headed protrusion or knob 4a there are also mounted by conventional injection molding techniques on the first cylindrical portion 3a a number of round headed protrusions 13 on the first cylindrical portion 3a. These knobs 13 and the second cylindrical portion 5a are made of a polymer material of preselected density to provide the desired elasticity and resistance to function as described herein below under the heading "Manner of Operation" (FIG. 15A). In the drawings 3 round headed protrusions or knobs 13 are shown arranged in a row. Obviously more or less knobs 13 and openings 14 can be provided and can be arranged differently from what has been illustrated without departing from the spirit of the invention.

Manner of Operation of the Second Embodiment

Figure 16A:
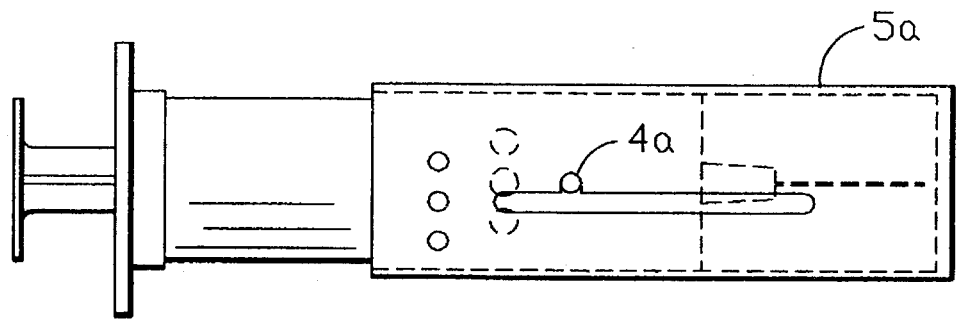
FIGS. 16A to 16D are four schematic views illustrating the syringe of the second embodiment of the invention in four different operative positions.
Figure 16B:
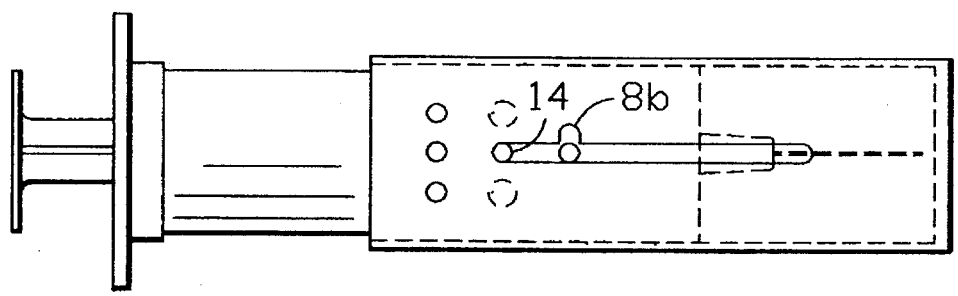
Figure 16C:
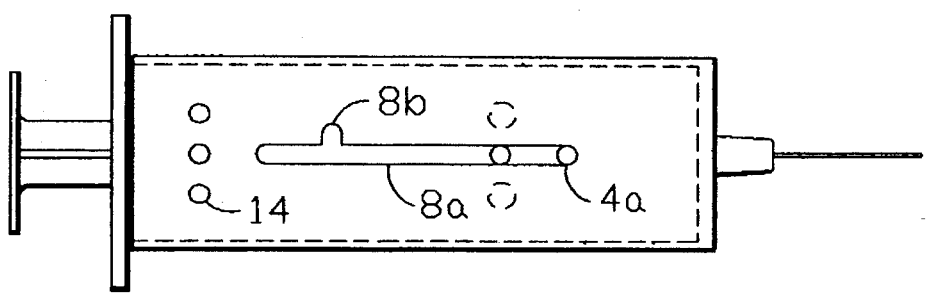
Figure 16D:
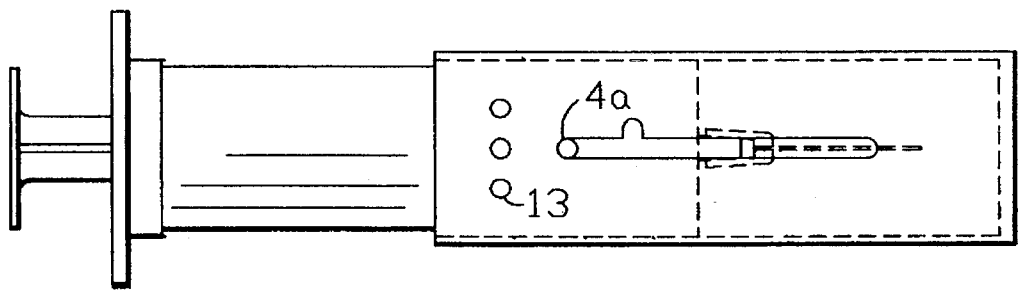

The second cylindrical portion is initially in a first extended position (see FIG. 16A) in which it fully envelopes the needle 2a so that no accidental pricking by the user can occur. Therefore in this second embodiment the standard plastic cap covering the needle 2a prior to use can be dispensed with because the second cylindrical 5a performs the functional equivalent of the plastic cap, i.e. preventing accidental pricking. As was the case with first embodiment the first cylindrical portion 3a, which forms part of the syringe itself, is made of a relatively heavy, high density polymer material, while the second cylindrical portion 5a is made of a lighter less dense polymer material which has a predetermined elasticity. As in the first embodiment the second cylindrical portion 5a has longitudinal slot 8a, into which the flat headed protrusion 4a projects, to guide the movement of the two cylindrical portions 3a, 5a relative to each other and to prevent any relative rotational movement between them. However, a short circumferentially extending slot is provided in slot 8b (FIG. 16B) is provided to permit the first flat headed protrusion 4a to be located in this slot 8a when the disposable syringe assembly has not yet been used and is preferably still stored in sterile plastic cover. The flat headed knob 4a together with the circumferential slot 8b therefore fixes the syringe assembly in this initial position. After the syringe has been removed from the plastic cover (not illustrated) a slight twist is imparted to the second cylindrical portion 5a relative to the first cylindrical portion 3a to longitudinally align the protrusion 4a with the longitudinal slot 8a (FIG. 16B). The second cylindrical portion 5a is now retracted relative to first cylindrical portion 3a. This movement of retraction is limited by the interaction of the pin (the flat headed protrusion) 4a with the longitudinal slot 8a and also by the abutting contact between the platform or collar 12a of the syringe and the rear end 9a of the second cylindrical portion 5a. In the fully retracted position the needle 2a has moved completely through the opening 7a in the bottom 6a of the second cylindrical portion 5a so that the syringe is ready for use (FIG. 16C). After the syringe has been used, the second cylindrical portion 5a is moved into a fully extended position by manually sliding it over the first cylindrical portion 3a until it reaches a forward limit position in which the protrusion 4a is in contact with rear end of the longitudinal slot 8a. In this position three auxiliary protrusions 13 snap into mating openings 14 in the second cylindrical portion 5a of the syringe (FIG. 16D) to further aid in fixing this position permanently and ready the used syringe for waste disposable. As can be noted from FIG. 16D in this final position the needle is fully and permanently enveloped so that no accidental pricking can occur.

While the invention has been described in detail by specific reference to preferred embodiments thereof, it is understood that variations and modifications may be made without departing from the true spirit and scope of the invention.

What is claimed is:

1. A disposable syringe, comprising in combination,
   a) a syringe body which includes a first cylindrical portion, a plunger axially movably reciprocally mounted in said cylindrical portion, a neck portion integral with said first cylindrical portion which extends outwardly from said first cylindrical portion at one end thereof, and a hypodermic needle which extends parallel to the longitudinal axis of said first cylindrical portion outwardly from said first cylindrical portion from the other end thereof; and
   b) a second cylindrical portion coaxially mounted on said first cylindrical portion; and second cylindrical portion having a bottom with an opening, said bottom being integral with said second cylindrical portion, said second cylindrical portion being first manually angularly movable and then manually slidably axially movable relative to said first cylindrical portion from a first partially extended position to a second fully retracted position; when said second cylindrical portion is disposed in said second fully retracted position said hypodermic needle projects through said opening in said integral bottom of said second cylindrical portion so that it is ready for use, and then said second cylindrical portion manually axially movable to a fully extended third position in which said bottom axially extends beyond the free end of said hypodermic to fully envelop said hypodermic needle; and
   c) first, second and third locking means on said first and second cylindrical portions to respectively operatively lock said second cylindrical portion in said first, second and third positions relative to said first cylindrical portion.

2. A disposable syringe, comprising in combination,
   a) a syringe body which includes a first cylindrical portion, a plunger axially movable reciprocally mounted in said cylindrical portion, said plunger having a neck portion which extends outwardly from said first cylindrical portion at one end thereof, and a hypodermic needle which extends outwardly from said first cylindrical portion from the other end thereof; and
   b) a first protrusion extending generally radially outwardly from said first cylindrical portion;
   c) a second cylindrical portion coaxially mounted on said first cylindrical portion and being manually slidably movable from a retracted position to an extended position; said second cylindrical portion having a front end with a bottom and an opening in said bottom, and an open rear end, said hypodermic needle projecting through said opening in the bottom of said second cylindrical portion when said second cylindrical portion is in the fully retracted position, said second cylindrical portion having a first longitudinal slot extending a predetermined distance parallel to the axes of the said first and second cylindrical portions and a second relatively short slot extending normally from said first longitudinal slot; the width of said first and second slots being slightly wider than the maximum width of said first protrusion; said first protrusion extending into said second short slot when said second cylindrical portion is in an initial partly extended position and being moved into alignment with said first longitudinal slot by manually rotating said second cylindrical portion a distance corresponding to the length of the second short slot prior to moving said second cylindrical portion into a fully retracted position;
   d) a plurality of second protrusions extending from said first cylindrical portion and a corresponding plurality of second mating openings in said second cylindrical portion; whereby
      i) said second cylindrical portion is initially in the first partly extended position and the hypodermic needle is fully disposed inside said second cylindrical portion, and
      ii) then said second cylindrical portion is slidably guidingly moved into a fully retracted position by the interaction of said first protrusion prior and said longitudinal first slot prior to use of the disposable syringe;
      iii) and then after the disposable syringe has been used the second cylindrical portion is moved into a second fully extended position in which the first protrusion is adjacent to the rear end of said first longitudinal slot, said plurality of second protrusions extend into the plurality of corresponding second mating openings and said hypodermic needle is fully disposed in said second cylindrical portion.

3. The disposable syringe as defined in claim 2, wherein said plurality of second protrusions are made of a polymer material which elastically deforms under pressure.

4. The disposable syringe as defined in claim 3, wherein said first cylindrical portion has a pair of collars respectively disposed at opposite ends thereof and extending from the cylindrical surface thereof; said second cylindrical portion slidably moving over said pair of collars as it is slidably manually moved over of said first cylindrical portion; said pair of collars defining an annular space between said first and second cylindrical portions.

5. The disposable syringe as defined in claim 4, wherein said first protrusion has an essentially flat radial outer surface and each one of said plurality of second protrusions have an essentially curved outer surface; said flat outer radial surface of said first protrusion is essentially radially coextensive with the outer surface of said first cylindrical portion and said curved outer surface of each one of said plurality second protrusions is essentially coextensive with the outer surface of said second cylindrical portion.

* * * * *